United States Patent
Zhu et al.

(10) Patent No.: US 10,947,518 B1
(45) Date of Patent: Mar. 16, 2021

(54) USING PROTEASES TO CONTROL RESTRICTION ENZYME ACTIVITY

(71) Applicant: ABclonal Science, Inc., Woburn, MA (US)

(72) Inventors: Zhenyu Zhu, Lynnfield, MA (US); Dapeng Sun, Lexington, MA (US); Aine Quimby, Newburyport, MA (US); Michaela Shottes, Methuen, MA (US)

(73) Assignee: ABclonal Science, Inc., Woburn, MA (US)

( * ) Notice: Subject to any disclaimer, the term of this patent is extended or adjusted under 35 U.S.C. 154(b) by 0 days.

(21) Appl. No.: 17/062,471

(22) Filed: Oct. 2, 2020

Related U.S. Application Data

(60) Provisional application No. 62/916,927, filed on Oct. 18, 2019.

(51) Int. Cl.
   *C12N 9/22* (2006.01)
   *C12Q 1/37* (2006.01)

(52) U.S. Cl.
   CPC .................. *C12N 9/22* (2013.01); *C12Q 1/37* (2013.01)

(58) Field of Classification Search
   None
   See application file for complete search history.

(56) References Cited

U.S. PATENT DOCUMENTS 5,204,238 A * 4/1993 Laue ...................... C12N 15/66
   435/199

OTHER PUBLICATIONS

Chica et al. CurrOpin Biotechnol. Aug. 2005;16(4):378-84. (Year: 2005).*
Singh et al. Curr Protein Pept Sci. 2017, 18, 1-11 (Year: 2017).*
Moran et al. FEMS Microbiology Letters 197 (2001) 59-63 (Year: 2001).*
Schierling et al. PNAS Jan. 26, 2010 107 (4) 1361-1366 (Year: 2010).*
Conlan et al. Biotechniques. Nov. 1999;27(5):955-60. (Year: 1999).*

* cited by examiner

*Primary Examiner* — Christian L Fronda
(74) *Attorney, Agent, or Firm* — Eric P. Mirabel

(57) ABSTRACT

Proteases are enzymes which hydrolyze protein enzymes, eliminating their activity. The present invention exploits the hydrolyzing activity of proteases including proteinase K, endoproteinase LysC and/or trypsin to control the activity of restriction enzymes and/or eliminate or reduce production of unwanted DNA or RNA fragments (known as star activity).

11 Claims, 10 Drawing Sheets

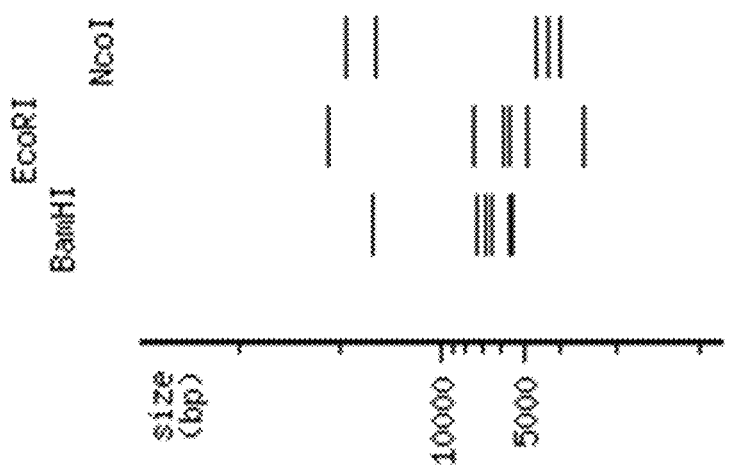
Fig. 1 Complete digestion pattern on lambda DNA

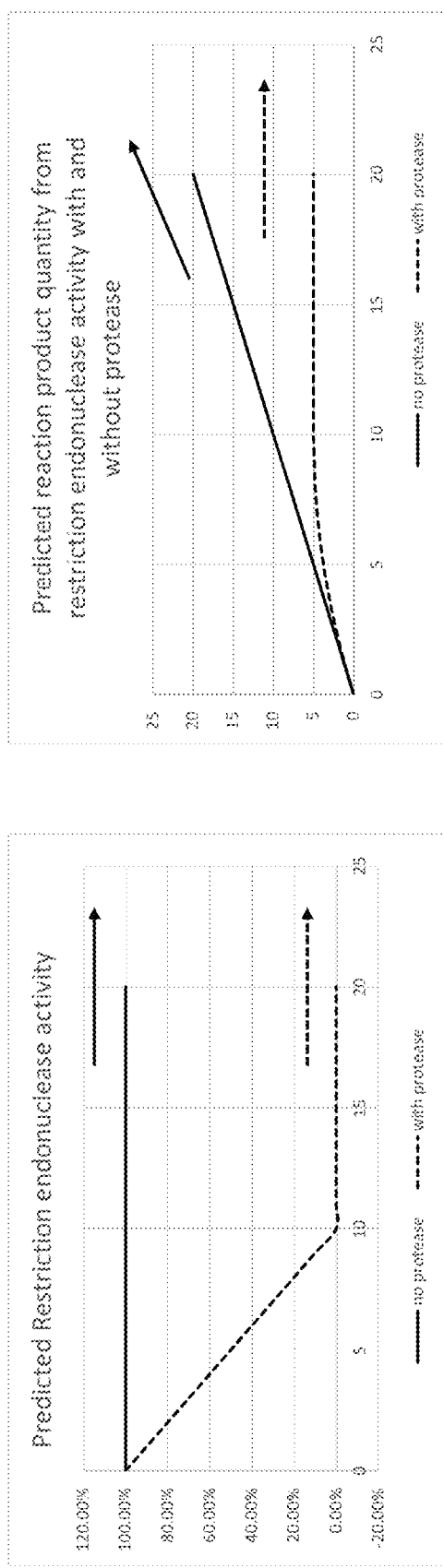
Fig 2: Predicted enzyme activity with and without addition of protease

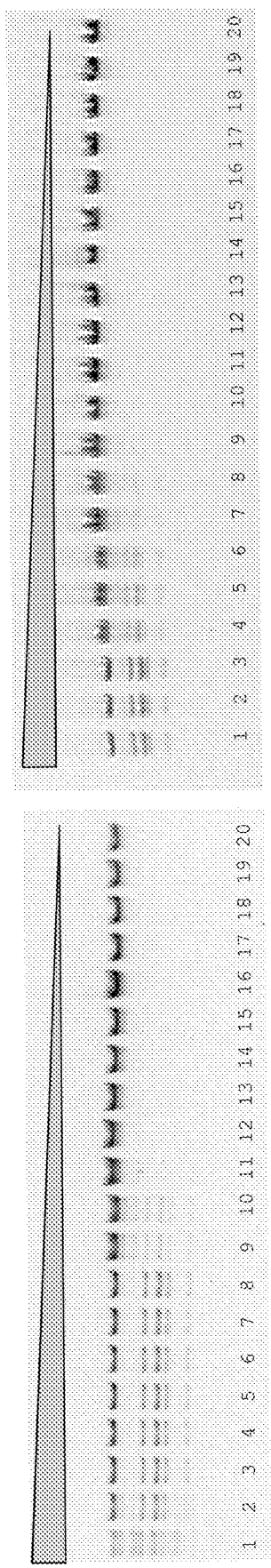
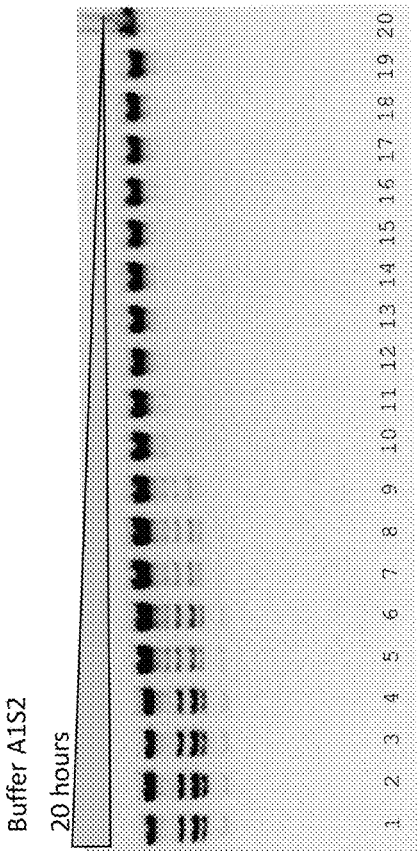
Fig. 3 EcoRI: Buffer A1 vs A1S2

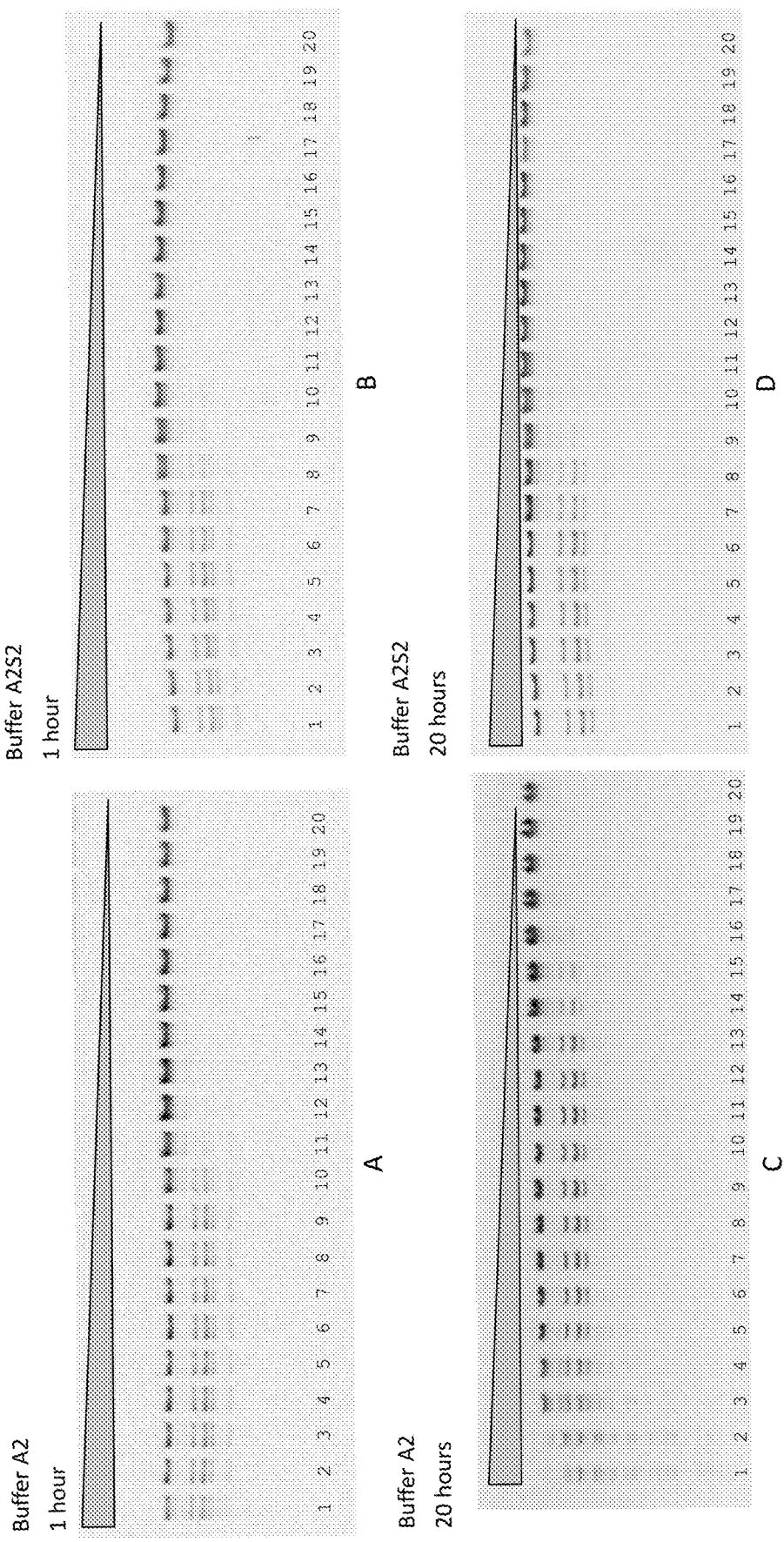

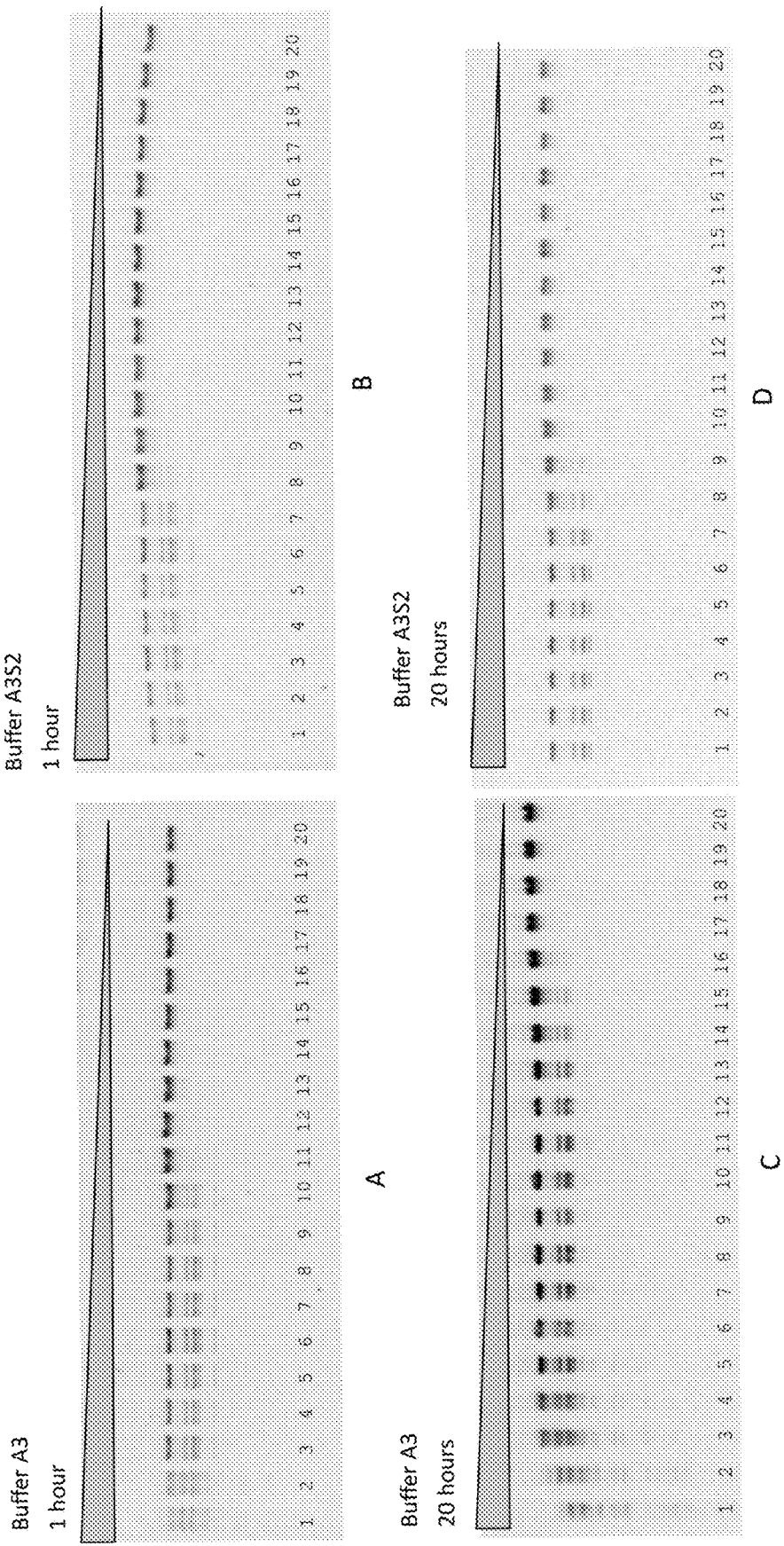

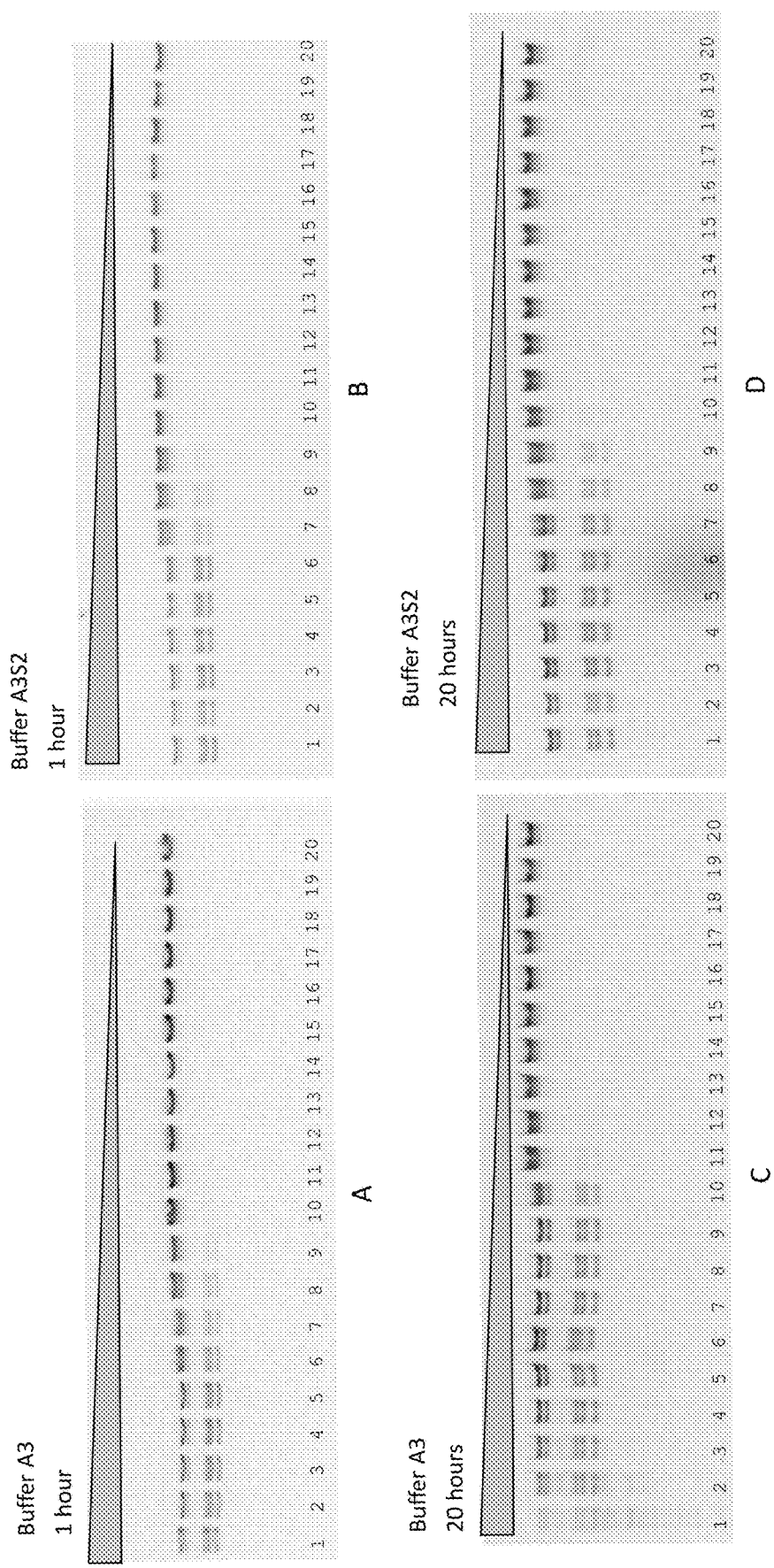

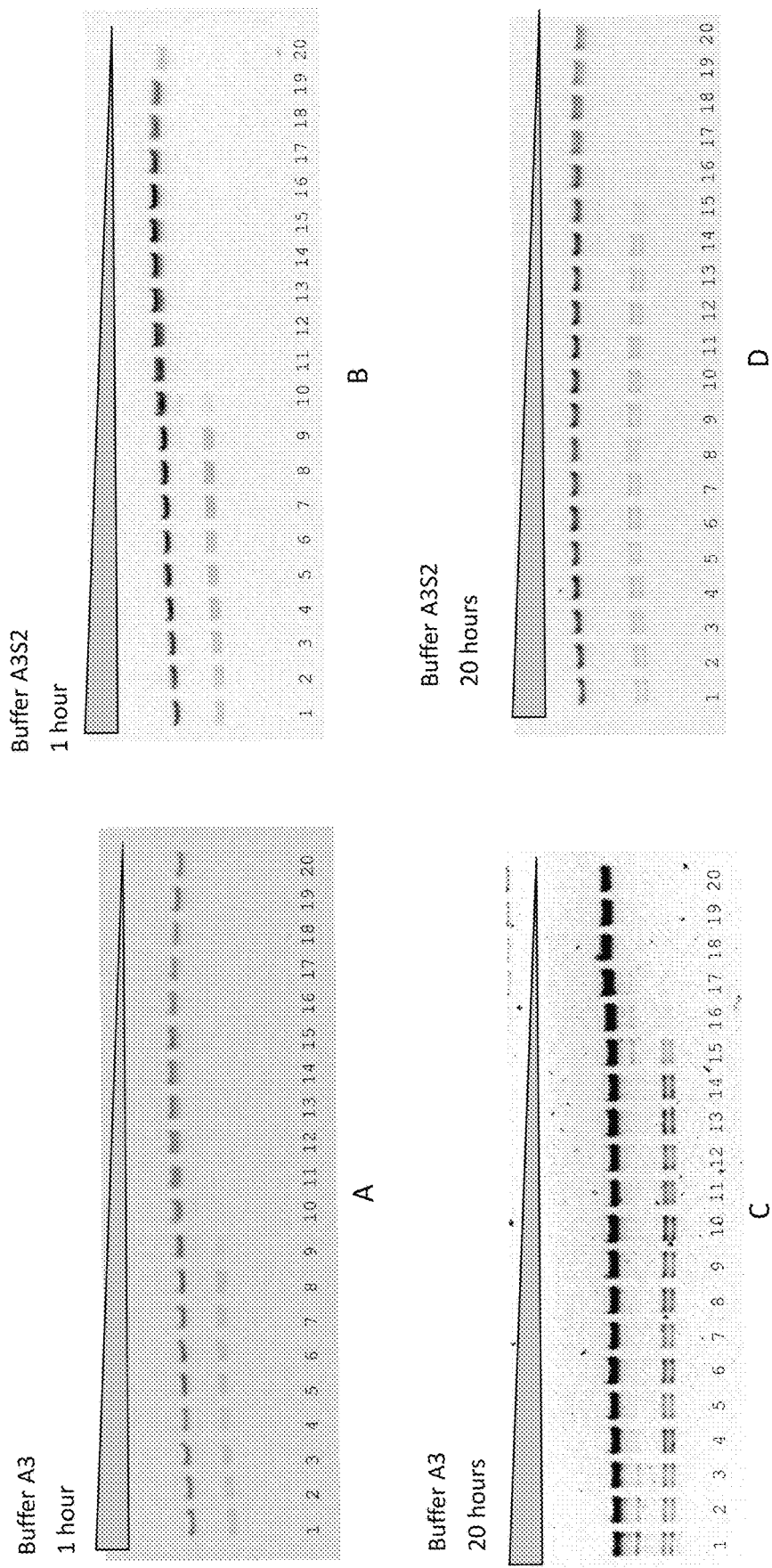

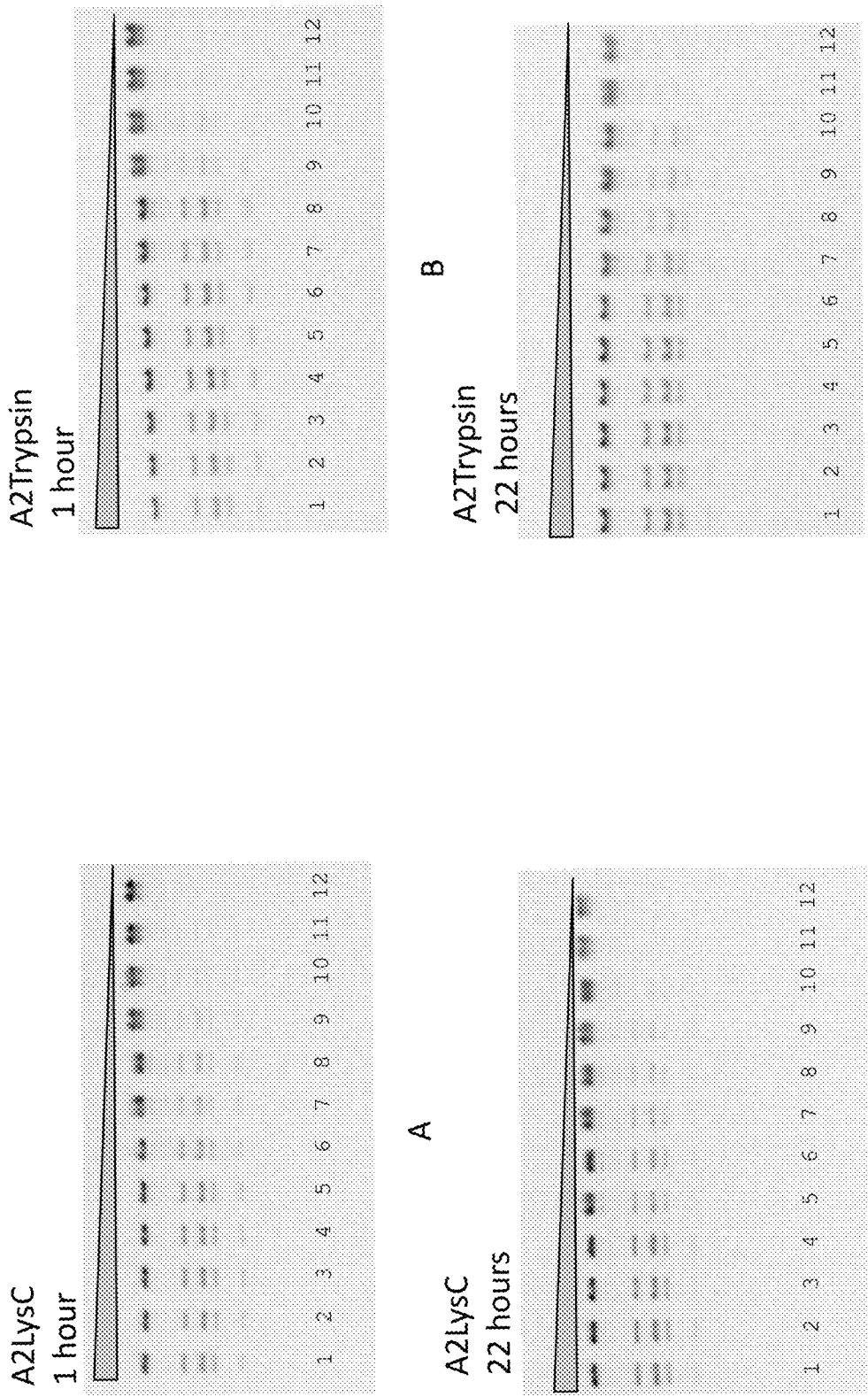

USING PROTEASES TO CONTROL RESTRICTION ENZYME ACTIVITY

BACKGROUND

Restriction enzymes, also known as restriction endonucleases, are a subclass of hydrolase enzymes that hydrolyze ester bonds, act as DNA or RNA nucleases and cleave specific DNA or RNA sequences. When performing an enzyme digestion reaction, the activity of all enzymes involved should be optimized for precision in obtaining the expected product or result. Most restriction enzymes catalyze the substrate (DNA or RNA) continuously over time, thus continuously accumulating the desired DNA or RNA fragments and occasionally, unwanted side products.

Though optimization of enzyme reactions with restriction endonucleases are usually attempted through specific buffer and reaction time conditions, there are sometimes undesired reactions and related problems, especially when enzyme displays off-target activity in addition to its main activity. Optimized restriction endonuclease activity typically digests a specified amount of substrate to completion within a set time. However, some restriction endonucleases generate side reactions and unwanted DNA or RNA cleavage with accumulated activity, especially with excess enzyme in a reaction, where the reaction continues for a long period, under particular buffer conditions, or where there is high glycerol. Such cleavage at sites other than the cognate restriction sites is known as star activity.

Controlling the concentration of enzyme or the overall reaction time, such as terminating the reaction via heat inactivation or other purification method when the reaction is completed, is a common method to limit total enzyme activity and thus reduce star activity. Other methods of controlling the reaction may be more desirable, particularly where fine control to achieve a higher reliability of the assay is desired.

SUMMARY

Proteases are enzymes which hydrolyze protein enzymes, eliminating their activity. The present invention exploits the hydrolyzing activity of proteases to control the activity of restriction enzymes and eliminate or reduce production of unwanted DNA or RNA fragments.

In this invention, proteases are initially included with or added at some point to the restriction endonuclease reaction mix, such that the restriction enzymes are inactivated by the protease during the course of their DNA/RNA digestion reaction. In this manner, total enzyme activity is controlled not only by buffers and reaction times, but also by the relative quantities of substrate, restriction endonucleases and proteases (and sometimes, including the protease addition time) in order to further limit over-digestion and star activity. Protease inhibitors can optionally be used to stop or inhibit protease activity at a desired point in the reaction.

The invention is further described in the figures and description which follow, including in the examples.

BRIEF DESCRIPTION OF THE FIGURES

FIG. 1: Theoretical complete pattern of BamHI, EcoRI and NcoI on lambda DNA according to the DNA sequence and enzyme recognition and cutting specificities. The pattern can be aligned with any of the bands shown in FIGS. 3-8 to indicate completion of cleavage and star activity.

FIG. 2: Panel A: Predicted intrinsic restriction endonuclease activity. Solid line: restriction endonuclease activity without proteases; dashed line, restriction endonucleases with proteases. Panel B: Total restriction endonucleases activity. Solid line: total restriction enzyme activity without proteases; dashed line, total restriction enzyme activity with proteases.

FIG. 3: The enzyme activity of EcoRI on lambda DNA in buffers A1 and A1S2. Panel A: 1 hour in buffer A1, Panel B: 1 hour in buffer A1S2, Panel C: 20 hours in buffer A1, Panel D: 20 hours in buffer A1S2. The descending triangle (top) represents the 2-fold serial dilution of the restriction endonuclease.

FIG. 4: The enzyme activity of EcoRI on lambda DNA in buffers A2 and A2S2. Panel A: 1 hour in buffer A2, Panel B: 1 hour in buffer A2S2, Panel C: 20 hours in buffer A2, Panel D: 20 hours in buffer A2S2. The descending triangle (top) represents the 2-fold serial dilution of the restriction endonuclease.

FIG. 5: The enzyme activity of EcoRI on lambda DNA in buffers A3 and A3S2. Panel A: 1 hour in buffer A3, Panel B: 1 hour in buffer A3S2, Panel C: 20 hours in buffer A3, Panel D: 20 hours in buffer A3S2. The descending triangle (top) represents the 2-fold serial dilution of the restriction endonuclease.

FIG. 6: The enzyme activity of BamHI on lambda DNA in buffers A3 and A3S2. Panel A: 1 hour in buffer A3, Panel B: 1 hour in buffer A3S2, Panel C: 20 hours in buffer A3, Panel D: 20 hours in buffer A3S2. The descending triangle (top) represents the 2-fold serial dilution of the restriction endonuclease.

FIG. 7: The enzyme activity of NcoI on lambda DNA in buffers A3 and A3S2. Panel A: 1 hour in buffer A3, Panel B: 1 hour in buffer A3S2, Panel C: 20 hours in buffer A3, Panel D: 20 hours in buffer A3S2. The descending triangle (top) represents the 2-fold serial dilution of the restriction endonuclease.

FIG. 8: The results of enzyme activity of EcoRI on lambda DNA. Panel A: 1 hour in buffer A2LysC, Panel B: 1 hour in buffer A2Trypsin, Panel C: 22 hours in buffer A2LysC, Panel D: 22 hours in buffer A3Trpsin. The descending triangle (top) represents the 2-fold serial dilution of the restriction endonuclease.

DETAILED DESCRIPTION

Figure 9:
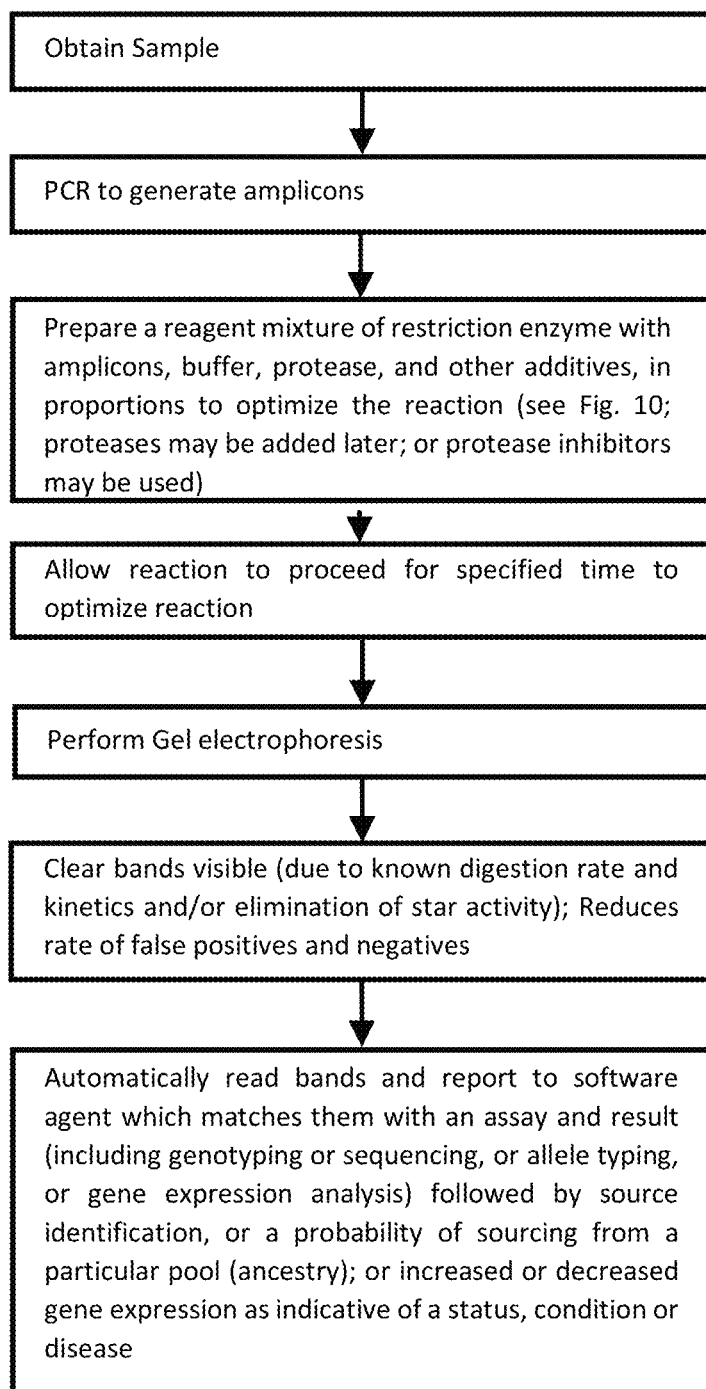
FIG. 9: Flow chart showing automated genotyping/sequencing/allele typing/gene expression analysis using the reagents and techniques of the invention.

Restriction enzymes which can be used in the invention include both endonucleases and catalytic RNAs (ribozyes), DNases and RNases. DNAases include a large number of enzymes which, based on their targets for cleavage, are further classified into Type I, Type II (where BamHI, EcoRI and NcoI in the examples below are Type IIP; palindromic), Type III, Type IV and Type V (e.g., the cas9-gRNA complex from CRISPR) as well as artificial restriction enzymes, which can target large DNA sites (up to 36 bp) and can be engineered to bind to desired DNA sequences. Zinc finger nucleases are the most commonly used artificial restriction enzymes.

Proteases can be classified into endopeptidases, which cleave the target protein internally, and exopeptidases— where carboxypeptidases digest amino acids from the carboxy-terminal end of a protein, and aminopeptidases digest proteins from the amino-terminus.

Proteases can further be classified based into seven broad groups, based on the catalytic residue used to facilitate proteolysis: serine proteases (using a serine alcohol as the catalytic residue); cysteine proteases (using a cysteine thiol as the catalytic residue); threonine proteases (using a threonine secondary alcohol as the catalytic residue); aspartic proteases (using an aspartate carboxylic acid as the catalytic residue); glutamic proteases (using a glutamate carboxylic acid as the catalytic residue); metalloproteases (using a metal, usually zinc, for catalysis); and, asparagine peptide lyases—using an asparagine to perform an elimination reaction (not requiring water).

Any of the foregoing proteases which prove suitable for controlling restriction enzyme reactions, including in order to reduce star activity (in addition to those in the examples below) can be used in the invention. Specific examples of proteases include: TEV protease, which is specific for the sequence ENLYFQ \S; trypsinogen; carboxypeptidase B; enterokinase; Lys-C and Thrombin.

Instead of including protease in the reaction mixture with the restriction endonuclease and the substrate, one can add the protease at a later time in the reaction process to inhibit or arrest nuclease activity. The timing of adding the components can also be optimized with routine experimentation.

Protease inhibitors include alpha 1-antitrypsin, alpha 1-antichymotrypsin, C1-inhibitor, antithrombin, plasminogen activator inhibitor-1, and neuroserpin. To control the protease portion of the reaction with an inhibitor, the inhibitor would need to selected so as to be one which inhibited the protease being used in the reaction to digest the restriction enzyme(s) used in the reaction. The protease inhibitor could be included with the reaction mixture or added at a later time, and it's addition would need to be optimized as part of optimization of the reaction process.

Specific examples of DNA-cleaving restriction endonucleases which can be used with the process of the invention (other than those in the examples below) include: HindIII, HincII, MutH, ExoRII, EcoR124I, EcoRV, EcoP151, Dnase1, Nuclease S1, Bal 31, DNAQ, Taq1, Not1, TREX1, TREX2 and WRN exonuclease. Specific examples of RNA-cleaving restriction nucleases which can be used in cleaving RNA with the process of the invention include endoribonucleases such as RNase III, RNase A, RNase H, RNase L, and RNase P; and exoribonucleases such as PNPase, RNase D, RNase R, and RNase T.

Among DNA restriction endonucleases which cleave at a unique recognition sequence: BamHI recognizes and cuts at G/GATCC; EcoRI recognizes and cuts at G/AATTC; and NcoI recognizes and cuts at C/CATGG. FIG. 1 shows the theoretical complete digestion pattern of BamHI, EcoRI and NcoI on lambda DNA, followed by gel electrophoresis. These three enzymes are used in the examples below, and the bands they generate in the examples can be compared to FIG. 1 for reference. Star activity is shown in FIGS. 3 to 8 (if present) as extra bands on the DNA gel in the left lanes (which represent high enzyme concentration).

Example 1

Schematic depiction of the enzymatic effect on substrate is shown in FIG. 2. In this example, the restriction endonuclease has very stable activity, maintaining 100% activity over time. Conversely, addition of protease, in this example, reduces restriction endonuclease activity by 10% per unit of time (i.e. per minute). After 10 time-units, there is no active restriction endonuclease remaining, as shown in Panel A. The accumulated restriction endonuclease activity is shown in panel B. While the total product of enzyme activity keeps increasing for the restriction endonuclease without protease, the reaction containing protease accumulates a limited amount of total activity, and then ceases.

In a formula to represent the activity of a stable restriction endonuclease, without protease, restriction endonuclease activity ($RE_A$) is consistently at 1.

$$RE_A=1$$

Total enzyme activity ($RE_T$) is determined over a time, designated with units T. With protease, restriction endonuclease activity ($RE_P$) is 1-0.1T when T is no more than 10, and zero when T is larger than 10.

$$RE_P=1-0.1T \text{ (when } T \text{ is no more than 10)}$$

The total activity ($RE_T$) is $0.5T-0.05T^2$ when T is no more than 10, and a constant 5 after T is larger than 10.

$$RE_T=0.5T-0.05T^2 \text{ (when } T \text{ is no more than 10)}$$

Since the simultaneous usage of protease controls the total output of the restriction endonucleases, it is referred to hereinafter as the internal protease control.

Example 2: The Internal Protease Control is Independent of Restriction Enzyme Reaction Buffers In this example, restriction endonuclease EcoRI, Diluent C, proteinase K, 6×STOP solution, and lambda DNA (substrate) were purchased from New England Biolabs. EcoRI is a highly active restriction endonuclease, which under certain circumstances (i.e. specific buffers) can have cleave at sites other than its cognate restriction sites, which is known as star activity. Proteinase K has broad specificity, predominantly cutting the peptide bonds adjacent to hydrophobic amino acids, and is active in wide range of buffers, so it can retain activity in a variety of reaction conditions including all restriction enzyme buffers, as long as there is no protease inhibitors Three different reaction buffers were tested in this example, with and without the addition of protease:

Buffer A1: 20 mM Tris-HCl, pH 7.4, 40 mM KoAc, 10 mM $MgCl_2$, 0.1 mM $CaCl_2$

Buffer A2: 20 mM Tris-HCl, pH 7.5, 40 mM NaCl, 10 mM $MgCl_2$, 0.1 mM $CaCl_2$

Buffer A3: 20 mM Tris-HCl, pH 8.0, 10 mM $MgCl_2$, 0.1 mM $CaCl_2$

Buffer A1S2: Buffer 1 plus 0.05 units/ml proteinase K

Buffer A2S2: Buffer 2 plus 0.05 units/ml proteinase K

Buffer A3S2: Buffer 3 plus 0.05 units/ml proteinase K.

EcoRI was serially diluted using Diluent C in 2-fold dilutions (where each successive lane in the figures represents a successive 2-fold dilution relative to the preceding lane). Digests of lambda DNA were performed in Buffer A1, Buffer A2, Buffer A3, and Buffer A1S2, Buffer A2S2, and Buffer A3S2. Reactions were stopped by adding 6×STOP solution at 1 hour or 20 hours.

In FIG. 3 using buffer A1: EcoRI can digest lambda DNA to completion at the $8^{th}$ lane but shows star activity between the $1^{st}$ to $3^{rd}$ lane at 1 hour. EcoRI can digest lambda DNA to completion through the $11^{th}$ lane but has star activity between the $1^{st}$ to $6^{th}$ lanes at 20 hours.

In FIG. 3 using Buffer A1S2: EcoRI can digest lambda DNA to completion through the $3^{rd}$ lane and has no star activity in any lanes at 1 hour. EcoRI can digest lambda DNA to completion through the 4$^{th}$ lane and has no star activity in any lanes at 20 hours.

In FIG. 4 using Buffer A2: EcoRI can digest lambda DNA to completion through the 9$^{th}$ lane but has star activity in the 1$^{st}$ lane at 1 hour. EcoRI can digest lambda DNA to completion through the 12$^{th}$ lane but shows star activity between the 1$^{st}$ to 5$^{th}$ lanes at 20 hours.

In FIG. 4 using Buffer A2S2, EcoRI can digest lambda DNA to completion through the 5$^{th}$ lane but has no star activity in any lanes at 1 hour. EcoRI can digest lambda DNA to completion through the 6$^{th}$ lane but shows no star activity in any lanes at 20 hours.

In FIG. 5 using Buffer A3, EcoRI can digest lambda DNA to completion through the 7$^{th}$ lane but shows no star activity at 1 hour. EcoRI can digest lambda DNA to completion through the 9$^{th}$ lane, but has star activity between the 1$^{st}$ to 4$^{th}$ lanes, at 20 hours.

In FIG. 5 using Buffer A3S2, EcoRI can digest lambda DNA to completion through the 6$^{th}$ lane but has no star activity in any lanes at 1 hour. EcoRI can digest lambda DNA to completion through the 6$^{th}$ lane but has no star activity in any lanes at 20 hours.

The results shown in FIGS. 3-5 show that addition of proteinase K changed the performance of EcoRI in all buffers A1, A2 and A3, which were re-named as buffer A1S2, A2S2, A3S2 respectively, when proteinase K was included.

Example 3: The Internal Protease Control Works with any Restriction Endonuclease All restriction endonucleases are proteins, and all proteins can be digested by proteinase K, thus the process is expected to be as effective on other restriction endonucleases as with EcoRI.

In addition to the EcoRI in Buffer A3 and A3S2 (see Example 2) two other restriction endonucleases were also tested: BamHI and NcoI (from New England Biolabs, Inc.)

BamHI and NcoI were each diluted with Diluent A (New England Biolabs, Inc.) in a 2-fold serial dilution, where the substrate was lambda DNA, and the buffers were Buffer A3 or A3S2. The reactions were stopped by adding 6×STOP solution at 1 hour and 20 hours respectively.

In FIG. 6 using Buffer A3: BamHI can digest lambda DNA to completion through the 7$^{th}$ lane and has no star activity at 1 hour. BamHI can digest lambda DNA to completion through the 9$^{th}$ lane but displays star activity between the 1$^{st}$ to 4$^{th}$ lanes at 20 hours.

In FIG. 6 using Buffer A3S2: BamHI can digest lambda DNA to completion through the 6$^{th}$ lane and has no star activity at 1 hour. BamHI can digest lambda DNA to completion through the 6$^{th}$ lane and has no star activity in any lanes at 20 hours.

In FIG. 7 using Buffer A3: NcoI can digest lambda DNA to completion through the 8$^{th}$ lane and has no star activity at 1 hour. NcoI digests lambda DNA to completion at 14$^{th}$ lane and has star activity between the 1$^{st}$ to 5$^{th}$ lanes at 20 hours.

In FIG. 7 using Buffer A3S2, NcoI can digest lambda DNA to completion through the 8$^{th}$ lane and has no star activity in any lanes at 1 hour. NcoI can digest lambda DNA to completion through the 13$^{th}$ lane but has no star activity in any lanes at 20 hours.

This example shows that in addition to EcoRI in Example 2, desirable enzyme activity of BamHI and NcoI can be changed by the addition of proteinase K.

Example 4: Internal Protease Control Using a Protease Other than Proteinase K

Proteinase K has a broad specificity for protein digestion and is active in most buffers. Other proteases, if active in the specific reaction buffer of the enzyme for the primary reaction, can substitute for proteinase K as the internal protease control.

Endoproteinase LysC is a serine endoproteinase that cleaves peptide bonds at the carboxyl side of lysine, and Trypsin is serine endoproteinase that cleaves peptide bonds at the carboxyl side of lysine or arginine.

Both enzymes were purchased from New England Biolabs.

Buffer A2LysC: Buffer A2 plus 400 ng/ml endoproteinase LysC.

Buffer A2Trypsin: Buffer A2 plus 25 ng/ml trypsin.

EcoRI was diluted with Diluent C in a serial 2-fold dilution, the substrate was lambda DNA, and digestion was performed in Buffer A2LysC or Buffer A2Trpsin. The reaction was stopped by adding 6×STOP solution at 1 hour and 22 hours respectively.

In FIG. 8 using Buffer A2LysC: EcoRI can complete the digestion of lambda DNA through the 5$^{th}$ lane at 1 hour with no star activity and can complete the digestion of lambda DNA through the 4$^{th}$ lane at 22 hours with no star activity. Using buffer A2Trpsin: EcoRI can complete the digestion of lambda DNA at 6$^{th}$ lane at 1 hour with no star activity and can complete the digestion of lambda DNA at 6$^{th}$ lane at 22 hours with no star activity.

This example shows that other proteinases capable of digesting restriction endonucleases can be used as the internal protease control for restriction endonucleases activity.

Applications for the Process of the Invention

The uses for the process of the invention include any application where nucleic acids are identified through their fragmentation patterns as captured using gel electrophoresis, and including DNA or RNA sequencing or genotyping, or allele typing, employing such identification means. Specific applications include biometric identification of tissue, blood or body fluid (living or not), or other sample donor identification in e.g., forensics or therapy; determination of ancestral information, and other research applications where a high degree of reliability is needed in identifying a nucleic acid source or its sequence. The process of the invention could also be used in gene expression analysis, where increased gene expression would present in the gel results as certain thicker and/or darker bands.

One method of automated sequencing, genotyping, allele typing or gene expression analysis of a sample using the reagents and processes of the invention is set forth in flow chart form in FIG. 9. The steps in FIG. 9 could be automatically performed (using e.g., a robot, which adds reagents at timed intervals from particular containers). In the last step, the gel results are automatically read and processed by a central processor capable of correlating them with known results, in order to identify the source of the sample or indicate the likely ancestry of the sample donor (based on presence of certain fragments following cleavage).

Optimization of Reaction

A general method for determining the proteases to use with particular restriction endonucleases, other than those exemplified below, is to perform the experiments set forth below in the examples with other combinations of proteases and restriction endonucleases, and with appropriate buffers, and perform the activity assay described and exemplified herein, with an appropriate level of serial dilution of restriction endonucleases as herein, to find the combinations of components which are best suited for particular functions, including finding those with attributes like most active per unit of restriction endonucleases and protease, and which can most effectively minimize star activity.

Certain restriction endonucleases or certain types thereof, are needed or preferred for certain functions, and those can be combined with compatible proteases, in compatible proportions and in appropriate buffers, all of which can be determined by routine experimentation following the same methods as used to find the combinations set forth in the examples below.

Figure 10:
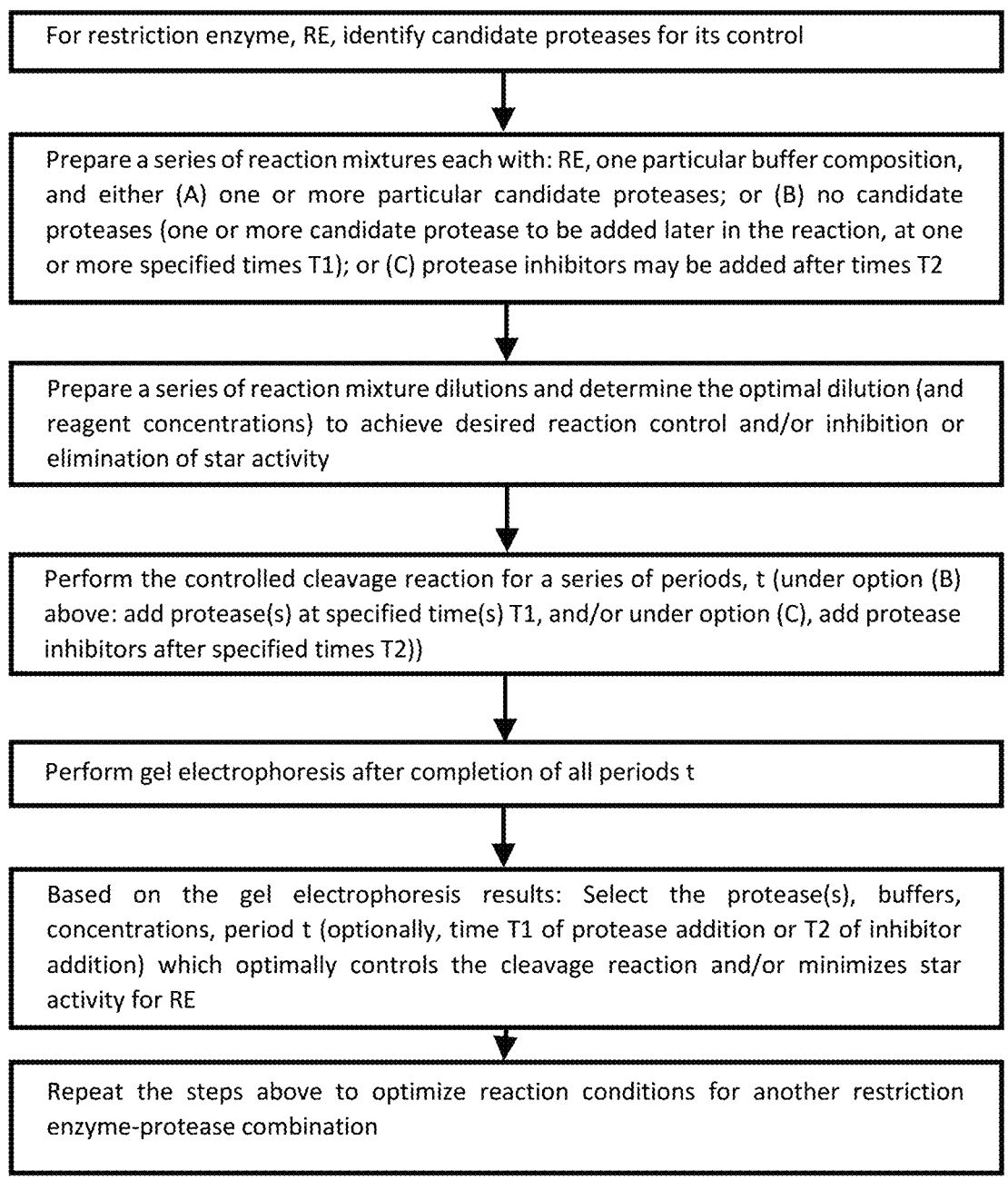
FIG. 10: Flow chart showing optimization of a restriction enzyme reaction where a protease is used to control it.

Other types of restriction enzymes which can be used in the invention include both protein endonucleases and catalytic RNAs (ribozyes), and both DNases and RNases. Similar experiments to those described herein can be performed to find suitable RNase/protease combinations for controlling RNase reactions and/or reducing star activity in such RNA-digesting reactions. When using an unknown restriction enzyme, RE, and one wishes to use protease to control the reaction or inhibit or eliminate star activity, the steps in the flow chart of FIG. 10 can be followed to optimize the reaction conditions. The steps in FIG. 10 track those set forth in FIGS. 3 to 8, which were used to determine the optimal reaction conditions for the restriction enzymes set forth there. One significant step is to perform a serial dilution to determine the optimal concentrations in the reaction mixture. The steps in FIG. 10 can be performed with each restriction enzyme, RE, one wishes to determine optimal conditions for use.

The specific processes, methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims.

It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process of inhibiting or preventing star activity by EcoRI comprising;
   digesting an oligomer using a reaction mixture including EcoRI, buffer and oligomer;
   including in the reaction mixture or adding proteinase K, endoproteinase LysC and/or trypsin to said reaction mixture in order to inhibit or prevent star activity by EcoRI; and
   terminating the digestion by adding a stopping solution including a loading dye.

2. The process of claim 1 wherein the oligomer is lambda DNA.

3. The process of claim 1 wherein the buffer is 20 mM Tris-HCl, pH 7.4, 40 mM KoAc, 10 mM $MgCl_2$, 0.1 mM $CaCl_2$; or 20 mM Tris-HCl, pH 7.5, 40 mM NaCl, 10 mM $MgCl_2$, 0.1 mM $CaCl_2$.

4. The process of claim 1 wherein the stopping solution includes 2.5% Ficoll®-400, 11 mM EDTA (pH 8.0), 3.3 mM Tris-HCl, 0.017% SDS, 0.015% bromophenol blue.

5. The process of claim 4 wherein 6× the stopping solution is added.

6. A process of determining the optimal relative concentrations to inhibit or prevent star activity by EcoRI, of EcoRI and a proteinase which is one or more of proteinase K, endoproteinase LysC or trypsin, comprising:
   (i) combining EcoRI and the proteinase, a buffer and an oligomer in order to achieve a starting concentration of each;
   (ii) determining the star activity of the EcoRI after a reaction time, and if there is any, diluting the reaction mixture and repeating the reaction for said reaction time;
   (iii) repeating step (ii) until there is no star activity; and
   (iv) determining the concentrations of the EcoRI and the proteinase at which star activity ceases.

7. The process of claim 6 wherein the proteinase is combined simultaneously with the restriction endonuclease.

8. The process of claim 6 wherein the oligomer is lambda DNA.

9. The process of claim 6 wherein the buffer is 20 mM Tris-HCl, pH 7.4, 40 mM KoAc, 10 mM $MgCl_2$, 0.1 mM $CaCl_2$; 20 mM Tris-HCl, pH 7.5, 40 mM NaCl, 10 mM $MgCl_2$, 0.1 mM $CaCl_2$; or, 20 mM Tris-HCl, pH 8.0, 10 mM $MgCl_2$, 0.1 mM $CaCl_2$.

10. The process of claim 6 wherein the restriction endonuclease activity is terminated by addition of STOP solution.

11. The process of claim 1 wherein the buffer is 20 mM Tris-HCl, pH 8.0, 10 mM $MgCl_2$, 0.1 mM $CaCl_2$.

* * * * *